US012594396B2

(12) United States Patent
Johnson et al.

(10) Patent No.: US 12,594,396 B2
(45) Date of Patent: Apr. 7, 2026

(54) VENTILATION METHODS AND DEVICES FOR TREATING RESPIRATORY DISEASES

(71) Applicant: CALIFORNIA INSTITUTE OF TECHNOLOGY, Pasadena, CA (US)

(72) Inventors: Michael R. Johnson, Pasadena, CA (US); Mary M. Easter, Pasadena, CA (US); Patrick Degrosse, Jr., Pasadena, CA (US); Brandon C. Metz, Pasadena, CA (US); George C. Richdale, III, Pasadena, CA (US); Ara Kourchians, Pasadena, CA (US); Havard F. Grip, Pasadena, CA (US); Noah T. Fox, Pasadena, CA (US); John Luke Wolff, Pasadena, CA (US); Evan W. Hilgemann, Pasadena, CA (US); Arthur J. Mastropietro, Pasadena, CA (US); Razmig Kandilian, Pasadena, CA (US); Daniel F. Berisford, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 880 days.

(21) Appl. No.: 17/905,158

(22) PCT Filed: Mar. 30, 2021

(86) PCT No.: PCT/US2021/024890
§ 371 (c)(1),
(2) Date: Aug. 26, 2022

(87) PCT Pub. No.: WO2021/206959
PCT Pub. Date: Oct. 14, 2021

(65) Prior Publication Data
US 2023/0122775 A1 Apr. 20, 2023

Related U.S. Application Data

(60) Provisional application No. 63/027,758, filed on May 20, 2020, provisional application No. 63/019,183, (Continued)

(51) Int. Cl.
*A61M 16/12* (2006.01)
*A61M 16/00* (2006.01)

(52) U.S. Cl.
CPC ........ *A61M 16/125* (2014.02); *A61M 16/024* (2017.08); *A61M 2202/0208* (2013.01); *A61M 2205/3334* (2013.01)

(58) Field of Classification Search
None
See application file for complete search history.

(56) References Cited

U.S. PATENT DOCUMENTS 3,913,607 A 10/1975 Price
3,977,432 A 8/1976 Vidal
(Continued)

FOREIGN PATENT DOCUMENTS

WO WO-2007071756 A1 * 6/2007 .......... A61M 16/205
WO 2021/216262 A1 10/2021

OTHER PUBLICATIONS

Non-Final Office Action for U.S. Appl. No. 17/905,161 filed on Aug. 26, 2022 on behalf of California Institute of Technology Mail Date: Jun. 3, 2025 12 pages.
(Continued)

*Primary Examiner* — Timothy A Stanis
*Assistant Examiner* — Thomas Z Chang
(74) *Attorney, Agent, or Firm* — Steinfl + Bruno LLP

(57) ABSTRACT

Ventilation methods and devices are described. The methods and devices can be used for treating respiratory diseases such as adult respiratory distress syndrome (ARDS).
(Continued)

Embedded control software managing various functionalities of the disclosed ventilators is also presented.

20 Claims, 10 Drawing Sheets

Related U.S. Application Data filed on May 1, 2020, provisional application No. 63/011,144, filed on Apr. 16, 2020, provisional application No. 63/011,080, filed on Apr. 16, 2020, provisional application No. 63/007,175, filed on Apr. 8, 2020.

(56) References Cited

U.S. PATENT DOCUMENTS

| | | | | |
|---|---|---|---|---|
| 4,474,477 | A | 10/1984 | Smith et al. | |
| 4,989,597 | A * | 2/1991 | Werner | A61M 16/104 |
| | | | | 128/203.14 |
| 6,279,574 | B1 | 8/2001 | Richardson et al. | |
| 8,939,129 | B2 | 1/2015 | Prinz et al. | |
| 2005/0222534 | A1 * | 10/2005 | Uesugi | A61M 13/003 |
| | | | | 600/156 |
| 2006/0124131 | A1 * | 6/2006 | Chandran | A61M 16/0666 |
| | | | | 128/206.28 |
| 2006/0144396 | A1 * | 7/2006 | DeVries | A61M 16/0057 |
| | | | | 128/204.26 |
| 2006/0153002 | A1 | 7/2006 | Ryan | |
| 2008/0264417 | A1 * | 10/2008 | Manigel | A61M 16/0063 |
| | | | | 128/205.12 |
| 2009/0201761 | A1 | 8/2009 | Matsuno et al. | |
| 2010/0224192 | A1 * | 9/2010 | Dixon | A61B 5/14539 |
| | | | | 128/204.23 |
| 2011/0197887 | A1 * | 8/2011 | Truschel | A61M 16/024 |
| | | | | 128/204.23 |
| 2014/0190481 | A1 | 7/2014 | Jam | |
| 2014/0190485 | A1 | 7/2014 | Milne et al. | |
| 2015/0007900 | A1 | 1/2015 | Li et al. | |
| 2015/0075524 | A1 | 3/2015 | Millar et al. | |
| 2016/0166795 | A1 | 6/2016 | Belsinger, Jr. et al. | |
| 2016/0287824 | A1 * | 10/2016 | Chang | A61M 16/204 |
| 2022/0100213 | A1 | 3/2022 | Huey et al. | |
| 2023/0121027 | A1 | 4/2023 | Johnson et al. | |

OTHER PUBLICATIONS

International Search Report and Witten Opinion for international PCT Application No. PCT/US2021/024890 filed on Mar. 30, 2021, on behalf of California Institute of Technology. Mail Date: Jul. 15, 2021. 9 Pages.

International Search Report and Witten Opinion for international PCT Application No. PCT/US2021/025238 filed on Mar. 31, 2021, on behalf of California Institute of Technology. Mail Date: Aug. 11, 2021. 14 Pages.

* cited by examiner

1

VENTILATION METHODS AND DEVICES FOR TREATING RESPIRATORY DISEASES

CROSS-REFERENCE TO RELATED APPLICATIONS

The present application is the U.S. National Stage of International Patent Application No. PCT/US2021/024890, filed on Mar. 30, 2021, which claims priority to US Prov. App. No. 63/007,175 filed on Apr. 8, 2020, US Prov. App. No. 63/011,080 filed on Apr. 16, 2020, US Prov. App. No. 63/011,144 filed on Apr. 16, 2020, US Prov. App. No. 63/019,183 filed on May 1, 2020 and US Prov. App. No. 63/027,758 filed on May 20, 2020, all of which are incorporated herein by reference in their entirety.

STATEMENT REGARDING FEDERALLY SPONSORED RESEARCH OR DEVELOPMENT

This invention was made with government support under Grant No. 80NM0018D004 awarded by NASA (JPL). The government has certain rights in the invention.

FIELD

The present disclosure is related to ventilation methods and devices, in particular for treating respiratory diseases. More in particular, it relates to methods and devices to treat victims of adult respiratory distress syndrome (ARDS).

BACKGROUND

The COVID-19 virus pandemic in 2020 is forecast to lead to a shortage of ventilators to assist in the treatment of those with compromised breathing and pneumonias in various areas of the United States. According to current statistics, virus can lead to a condition of ARDS (Adult Respiratory Distress Syndrome) in approximately 20% of those who are infected.

ARDS is a condition that may occur within the lung in response to a variety of injuries be they trauma, aspiration, or a variety of pneumonias—viral, bacterial, or fungal.

The challenge in treating these patients is not only to supply increasing amounts of oxygen, but to provide enough mechanical assistance/augmentation of that appropriate gas mixture to inflate lungs where the compliance or stiffness of the lungs may require more than double the amount of pressure applied just to get an adequate amount of air into the lungs to inflate them and get rid of carbon dioxide while meeting the body's oxygen requirements as well.

Various estimates forecast that, given a worst-case scenario, the current pandemic would likely result in rapidly overwhelming the worldwide supply of ventilators in acute care facilities To appreciably impact the dearth of available devices, practical designs are required that may be rapidly constructed, deployed, and operated with minimal training. Existing ventilator systems use thousands of parts, with correspondingly complex control software.

SUMMARY

The disclosed methods and devices provide practical solutions to the above-mentioned problems, and address, for example, the challenge of providing safe, reliable operation for patients with COVID-19 while requiring a minimum of sophisticated, costly components in the ventilation device.

The teachings of the present disclosure offer a readily constructed, inexpensive ventilator designs that are suitable for mass production using easily available parts and technologies. The disclosed methods and devices were conceived with priority placed on simple, robust construction; wide availability of components; minimal component count; minimal need to clean and sterilize equipment to facilitate rapid reuse between patients.

According to a first aspect of the present disclosure a lung ventilator is provided, comprising: a blender, and a pressure/flow generator section comprising a first pressure regulator and a second pressure regulator; wherein: the blender is configured to separately receive oxygen in a regulated oxygen flow from an oxygen source and air in a regulated air flow from an air source, and to blend the oxygen and the air to generate a fluid mixture; the pressure/flow generator section is configured to receive the fluid mixture from the blender and to generate through the first pressure regulator a first mixture having a first pressure and through the second pressure regulator a second mixture having a second pressure, the first pressure being a peak inspiratory pressure (PIP) and the second pressure being a positive end-expiratory pressure (PEEP).

According to a second aspect of the present disclosure a lung ventilator is provided, comprising: a blender; a pressure/flow generator section; and an electro-pneumatic regulator operatively coupled with the pressure/flow generator section, wherein: the blender is configured to separately receive oxygen in a regulated oxygen flow from an oxygen source and air in a regulated air flow from an air source, and to blend the oxygen and the air to generate a fluid mixture; the pressure/flow generator section is configured to receive the fluid mixture from the blender; and the electro-pneumatic regulator is configured to control a desired pressure level of the fluid mixture to be supplied to a patient during inspiration and the expirations phases.

According to a third aspect of the present disclosure, a lung ventilator is provided comprising: a blower, and an input plenum connected to the blower; wherein: the lung ventilator is configured to receive oxygen in a regulated oxygen flow from an oxygen source and to fluidically transmit the oxygen to the input plenum; in operative conditions the blower is in a powered state, thereby generating a negative pressure inside the input plenum to draw ambient air inside the input plenum; the input plenum is configured to receive the oxygen thereby blending the oxygen and the ambient air inside the plenum to generate a gas mixture; and the blower is configured to transmit the gas mixture based on a desired pressure.

According to a fourth aspect of the present disclosure, a medically assisted, machine regulated breathing method is disclosed, comprising: blending oxygen and air to generate a fluid mixture; from the fluid mixture, generating a first mixture with a peak inspiratory pressure (PIP) and a second mixture with a positive end-expiratory pressure (PEEP); during an inspiration phase: delivering the first mixture to a patient, measuring flow rate to calculate a tidal volume, and adjusting the flow rate to match the tidal volume with a desired tidal volume; during an expiration phase: blocking the first mixture to let the second mixture flow provide a plateau pressure; expelling gas exhaled from the patient to the outside; measuring pressure at the patient side; and triggering inspiration when the pressure at the patient side is less than PEEP.

Further aspects of the disclosure are provided in the description, drawings and claims of the present application.

DETAILED DESCRIPTION

Provided herein are some definitions of various terms used throughout the present disclosure:

Tidal volume—Volume of air delivered to the patient's lung, usually in milliliters (mL)

Peak inspiratory pressure (PIP)—Maximum pressure delivered to the patient's airway during the inhalation phase, usually in centimeters of water (cmH2O).

Positive end-expiratory pressure (PEEP)—Minimum pressure of the air delivered to the patient's lung, usually in centimeters of water (cmH2O).

Respiratory rate—Rate of patient breathing, usually in breaths-per-minute (bpm).

FiO2 (Fractional Inspired Oxygen)—Percentage of inspired air that is oxygen, usually ranging from 21% to 100%.

Plateau pressure—Pressure in the patient airway at the end of an inspiration phase when the flow of air into the lungs is zero and before the expiration phase starts. This pressure represents the actual obtained pressure within the lungs when all flow resistance pressure losses are zero.

Figure 1:
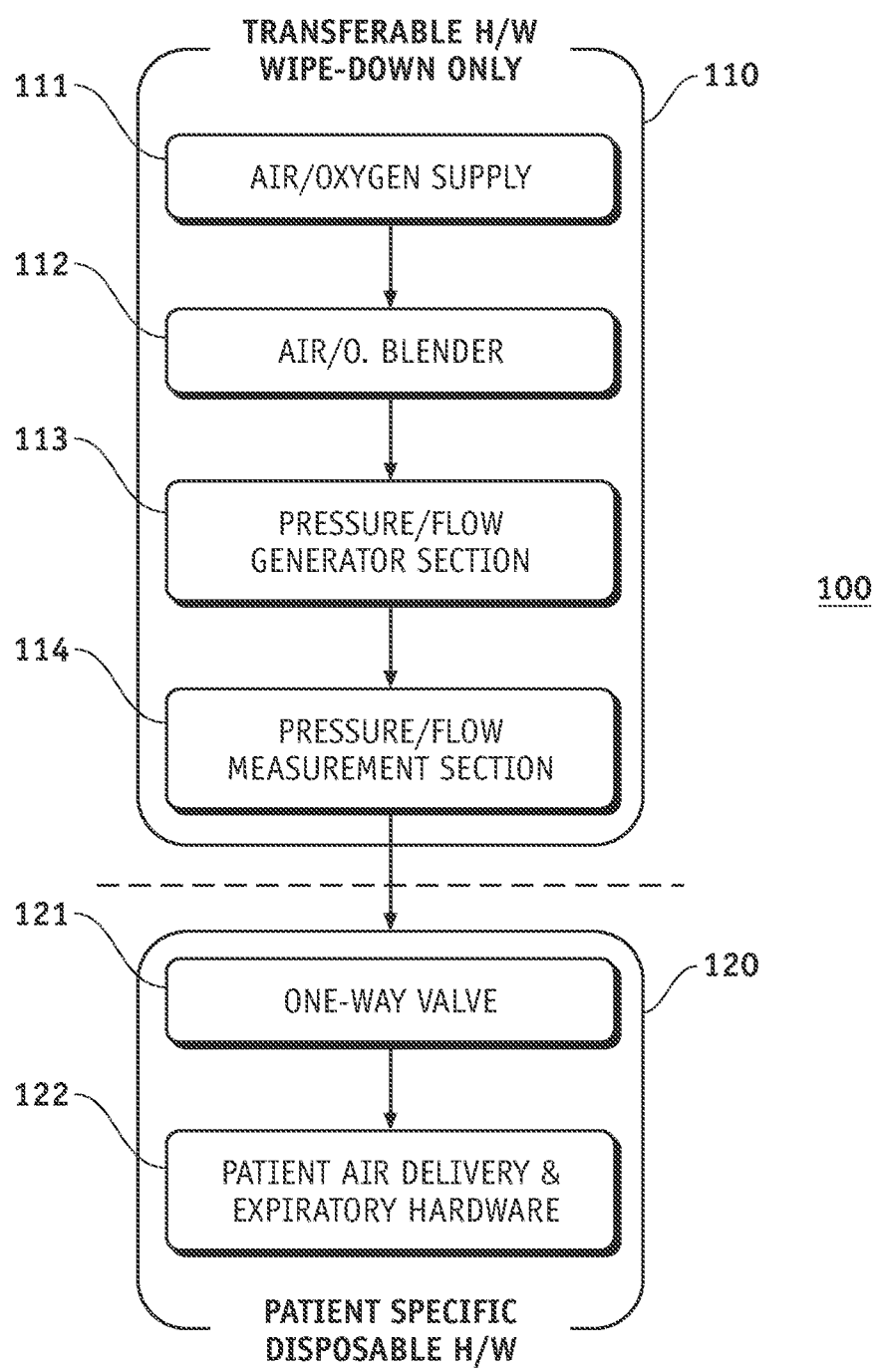
FIG. 1 shows a high-level block diagram of a medical system in accordance with an embodiment of the present disclosure.

FIG. 1 shows an exemplary medical system (100) in accordance with embodiments of the present disclosure. Medical system (100) comprises a ventilator (110) and a patient-specific device (120) attaching ventilator (110) to the patient. Ventilator (110) comprises air/oxygen blender (112), pressure/flow generation section (113), and pressure/flow measurement section (114). During normal operative conditions, ventilator (110) is essentially used to move air into and out of the patient's lungs (oxygen in and carbon dioxide out). Such function is performed by going through periodic cycles, each comprising an inspiration and an expiration phase. In accordance with the teachings of the present disclosure, patient-specific device (120) is detachable from ventilator (110).

Ventilator (110) receives oxygen and air from the air/oxygen supply (111). As will be described more in detail later, the required air and oxygen may be sourced either from an external supply or from the treatment facility. Supplied air and oxygen are then blended by the air/oxygen blender (112). Throughout the inspiration phase, pressure/flow generation section (113) is in an inspiration state and constantly provides the regulated pressure needed to provide the mixture to the patient. Such mixture is received by the patient through the patient-specific device (120) which comprises one-way valve (121) and patient air delivery and expiratory hardware (122).

During the inspiration phase, the flow rate and the pressure of the mixture output to the patient are measured by pressure/flow generation section (113). When the tidal volume is reached, the state of pressure/flow generation section (113) changes to a zero flow (plateau) condition where the plateau pressure is measured by pressure/flow measurement section (114). After such measurement, the inspiration phase time ends and the expiration phase begins. During the entire expiration phase, pressure/flow generation section (113) provides a constant PEEP pressure. The expiration phase may end either when the expiration phase time ends, or when a spontaneous inspiration initiated by the patient occurs.

In accordance with embodiments of the present disclosure, expiratory gas is not sent back to ventilator (110). As such, only the one-way valve (121), and some constituents of the patient air delivery and expiratory hardware (122) may be disposed after use by each patient. By virtue of providing such a feature, the cleaning and sterilization protocol is minimized to facilitate rapid reuse between patients and the transfer time from one patient to another can be drastically decreased from hours to minutes.

Figure 2A:
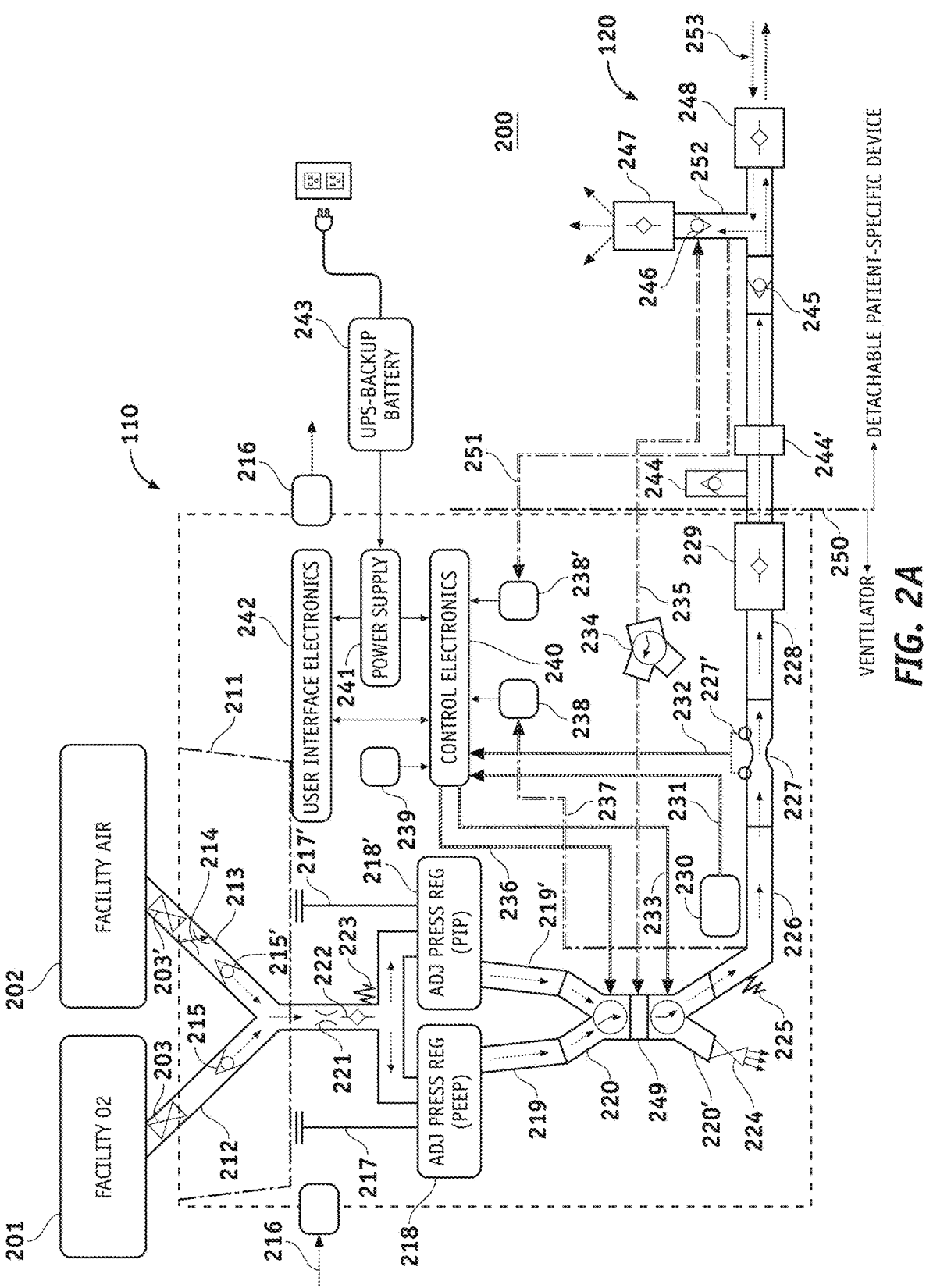
FIG. 2A shows an exemplary medical system according to a pneumatic type embodiment of the present disclosure.
Figure 2B:
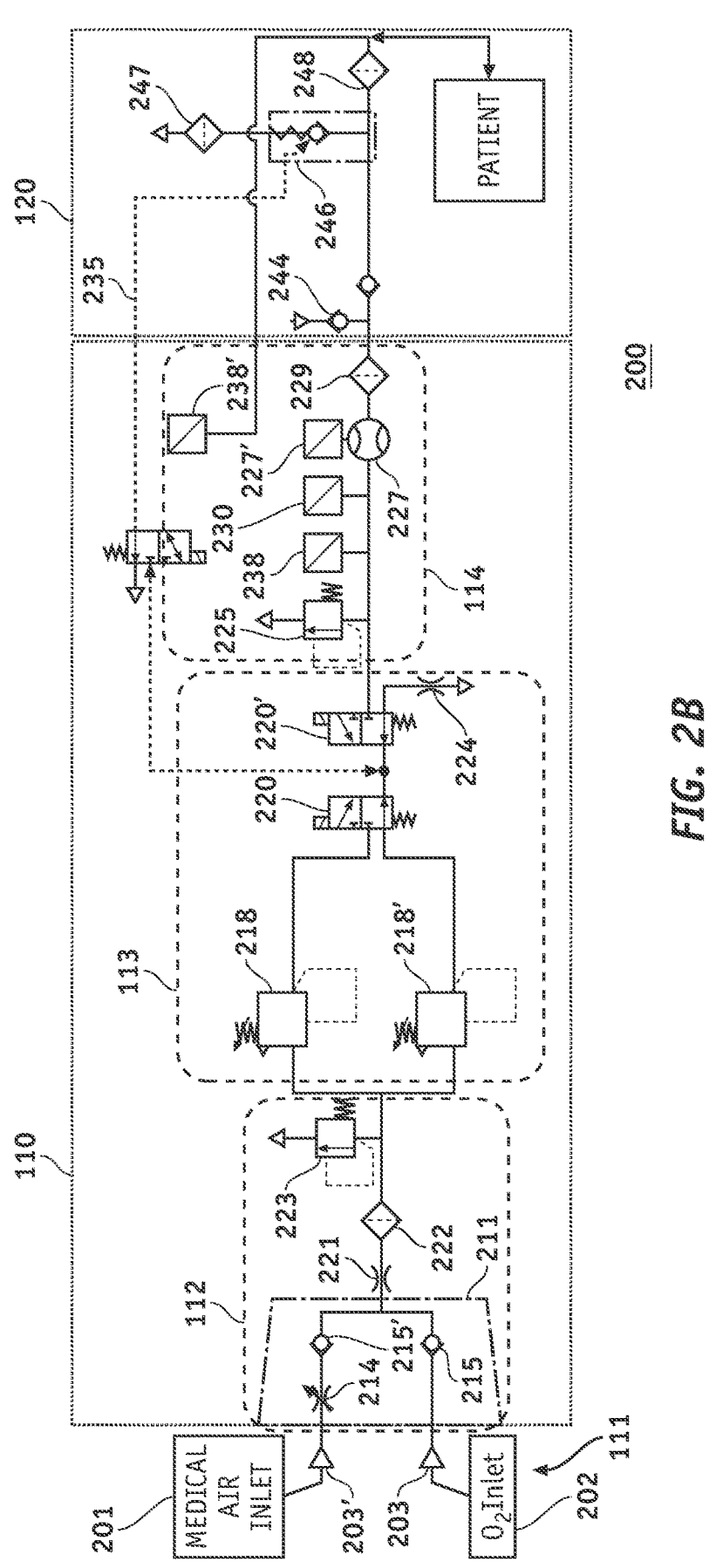
FIG. 2B shows the fluid schematic diagram of the exemplary medical system of FIG. 2A.

FIG. 2A shows an exemplary medical system (200) in accordance with an embodiment of the present disclosure. The fluid schematic diagram of the medical system (200) is shown in FIG. 2B. As FIG. 2B represents a fluid schematic diagram, some of the elements shown in FIG. 2A are not shown in FIG. 2B. Elements (110-114, 120-122) of FIG. 1 together with their constituents are also shown in FIG. 2B. In what follows, a detailed description of the constituents of ventilator (110) and patient-specific device (120) will be provided.

With reference to FIGS. 2A-2B, oxygen and air are provided by facility oxygen (201) and facility air (202) which may essentially comprise high-pressure bottles supplied by the treatment facility. The supplied oxygen and air are regulated by medical oxygen regulator (203) and air regulator (203') respectively. The regulated oxygen and air are then blended by air/oxygen blender (112) which comprises a blending section (211) including tubes (212, 213) through which air and oxygen can flow downstream. The blended gas is then applied to two separate pressure regulators, i.e. PEEP pressure regulator (218) and PIP pressure regulator (218') which can be adjusted using, e.g., manual knobs (217, 217'), respectively. For a normal operative condition, manual knobs (217, 217') may be adjusted such that the mixtures flowing in tubes (219, 219') have low and high pressure respectively. The low and high pressures values may be selected in correspondence with the PEEP and PIP pressures respectively. By way of example and not of limitation, the PEEP pressure (low) may be within a range of 5-20 cm H2O, while the PIP pressure (high) may be set to be 35 cm H2O above the PEEP pressure.

With further reference to FIGS. 2A-2B, ventilator (110) further comprises a first 3-way selector valve (220) connected to a second 3-way selector valve (220') via hose (249). Throughout the inspiration phase, the first and second 3-way selector valves (220, 220') are in closed position, thereby selecting high pressure mixture to be supplied to the patient. First and second 3-way selector valve (220, 220') are in the open state during the expiration phase. To this effect, ventilator (110) further comprises control electronics (240) connected to the first and second 3-way selector valves (220, 220') through electrical connections (236, 233) respectively, thereby controlling the state of both 3-way valves in correspondence with the inspiration and expiration phases as mentioned above. Coming out of the second 3-way selector valve (220'), the mixture will exit pressure/flow generation section (113) (see FIGS. 1 and 2B) to enter pressure/flow measurement section (114) before reaching patient-specific device (120). Ventilator (210) further comprises a user interface including displays and buttons (not shown) which are controlled by user interface electronics (242) which is, in turn, under control of the above described control electronics (240).

With continued reference to FIGS. 2A-2B, pressure/flow measurement section (114) of the ventilator (110) comprises FIO2 sensor (230), FIO2 sensor manifold (226), differential pressure flow sensor (227'), differential pressure flow sensor manifold (227), hose (228), bacterial/viral filter (229), static pressure sensor (238), and plateau pressure sensor (238'). In general, the flow and pressure sensors provide telemetry for decision-making in control electronics (240). The FIO2 sensor (230) is placed at sensor manifold (226) to measure the percentage of the oxygen in the inspired air that may be required to be, for example, within a desired range of 21%-100%. Such measured percentage is sent to control electronics (240) via electrical connection (231) and then communicated to user interface electronics (242) to be displayed. Based on the displayed measurement, the operator may decide to change the oxygen level by way of adjusting a knob (not shown) connected to an adjustable orifice (214) inside tube (213) of the blending section (211). Adjustable orifice (214) may be a variable diameter orifice that can adjust the air flow such that the resulting percentage of the oxygen in the mixture will equal to the desired value based on the position of the knob set by the operator. Differential pressure flow sensor (227') is in contact with differential pressure flow sensor manifold (227) and is used to measure the differential pressure from which the flow rate is derived and sent to the control electronics (240) through electrical connection (232). The inspirational flow rate should be such that the integral of the inspiratory flow rate over the inspiration time matches the desired tidal volume set by the operator through the user interface. The tidal volume may have, for example, a maximum value of 800 cc.

With continued reference to FIGS. 2A-2B, static and plateau pressure sensors (238, 238') are mounted on control electronics (240). Static pressure sensor (238) is connected to an end of sensor manifold (226), where the flow is stagnant, via hose (237). The static pressure is the actual pressure that the physician or operator wants to operate the system at for the patient's therapy. This is set by the physician or operator through the user interface. During the inspiration phase, if the measured static pressure is different from the desired static pressure set by the operator, an alarm located in the user interface electronics (242) is triggered.

Before entering the patient-specific device (120), the mixture is applied, after flowing through hose (228), to bacterial/viral filter (229) which is used to filter out possible pathogens in the mixture.

With further reference to FIGS. 2A-2B, the patient-specific device (120) generally comprises safety valve (244), one-way valve (245), expiratory valve (246) placed in expiratory tube (252), and external viral/bacterial filter (247). The patient-specific device (120) may also optionally include either a humidifier (244') or a heat moisture exchange filter (248), but usually not both at the same time. During the inspiration phase, the mixture provided by ventilator (210) is pushed to the patient's lung via patient tube (253). The exhaled gas coming from the patient's lung throughout the expiration phase flows through patient tube (253) to expiratory tube (252) before exiting the system to the outside atmosphere.

Ventilator (110) of FIGS. 2A-2B further comprises pilot hose (235) which essentially functions as a control hose. Pilot hose (235) is connected, at a first end, to hose (249) and at a second end, to expiratory valve (246). Due to such connections, during the inspiration phase, the pilot hose (235) carries the same high pressure as the mixture of oxygen/air pressure within hose (249) and as a result, expiratory valve (246) at the second end of pilot hose (235) is in a closed/OFF state not allowing any gas flowing out of the system. On the other hand, during the expiration phase, the mixture pressure within hose (249) and therefore within pilot hose (235) is low, and as a result, the expiration valve is in an open/ON state allowing the exhalated gas from the patient's lung to exit to the outside environment. The person skilled in the art will understand that during the expiration phase, one-way valve (245) will not allow any exhaled gas from the patient side to enter the system. The exhaled gas is applied to viral/bacterial filter (247) before entering the outside environment to ensure that possible unwanted pathogens are filtered out. Pilot hose (235) comprises a pilot 3-way valve (234) which is in the closed state during both the inspiration on expiration phase. The only time pilot 3-way valve (234) goes to an open state is in case of a failure where the gas will be let out of pilot hose (235), thereby allowing the patient exhale. In view of what was described above, when transitioning from the inspiration (high pressure) to the expiration (low pressure) phase, the pressure within pilot hose (235) needs to be relieved. This function is essentially performed by the second 3-way valve (220'). When transitioning from the inspiration to the expiration phase, through control signals received by control electronics (240) as described before, the state of the second 3-way valve (220') changes from closed to open. As a result, extra air within pilot hose (235) is let out to the outside environment and via bleed orifice (224), thus reducing the pressure within pilot hose (235).

The plateau pressure represents the pressure provided by medical system (200) of FIGS. 2A-2B in the patient airway at the end of an inspiration phase when the flow of air into the lungs is zero. In accordance with the teachings of the present disclosure, at the end of the inspiration phase, the plateau measure is measured and reported to control electronics (240). The plateau pressure measurement is performed by the plateau pressure sensor (238') connected to expiratory tube (252) through plateau tube (251). The plateau pressure measured value is displayed at the user interface for the operator's attention. An alarm is triggered if the measured value is outside the desired range.

Turning now back to blender (211) of FIGS. 2A-2B, tubes (212, 213) may include check valves (215, 215') respectively. Such check valves require certain cracking pressures to open and let the air and oxygen flow. By way of example and not of limitation, such pressure values for check valves (215, 215') may be 5 psi and 0.1 psi respectively. Ventilator (110) may further comprise orifice (221), particulate filter (222), and relief valves (223, 225). Orifice (221) may be a 0.063" orifice, its role being that of limiting the flow of the mixture in the case there is a downstream failure. Particulate filter (222) may be a 90 um filter which is used to filter out unwanted particulates from the oxygen/air mixture. According to an embodiment of the present disclosure, relief valve (223) may be a 100 psi valve protecting the system from potential damages in cases where the system is mistakenly hooked up to high levels of pressure that are not tolerable by the system. Relief valve (225) may be a 1 psi relief valve used as a safety valve for the downstream side of the system to ensure that the pressure of the oxygen/air mixture provided to the patient stays below a safe limit.

As mentioned previously, the input to medical system (200) is a pressurized source of medical air and a pressurized source of oxygen. The input pressures may be, for example, at 50 psi, plus or minus 5 psi. The input pressure range may be selected within a range from 30 to 100 psi for each of the gasses. In accordance with the teachings of the present disclosure, check valve (215) has a higher cracking pressure than check valve (215'). With the gasses connected and adjustable orifice (213) closed, the flow will be from the oxygen source only and 100% oxygen will be delivered to the ventilator. As adjustable orifice (213) is opened, some air is allowed to flow into the gas pathways and mix with the oxygen. This lowers the oxygen percentage level in the blended air. As adjustable orifice (213) is opened more, the air flow increases until the flow is dominated by the medical air. The medical air has priority over the oxygen in the full open condition because the oxygen input check valve (215) has a higher pressure drop than the medical air input check valve (215'). This means the medical air has enough pressure authority to close the check valve (215) in the oxygen input line and provide only medical air.

Details of the flow pressure drop of adjustable orifice (213) affect the amount of the pressure authority the medical air input has over the oxygen input. The input pressure difference also affects this authority. A lower authority will mean the blender (211) will not be able to get down to the lowest value, e,g. 21% oxygen. How low the oxygen level can go to is determined by the details of the flow losses in the check valves (215, 215'), the adjustable orifice (213), and the input pressure difference. Ventilator (110) of FIGS. 2A-2B further comprises a power supply (241) feeding the control electronics (240) and the user interface electronics (242). Power supply (241) is connectable to a pluggable UPS-back up battery (243). Ventilator (110) further comprises a fan (216) for cooling purposes.

Figure 3A:
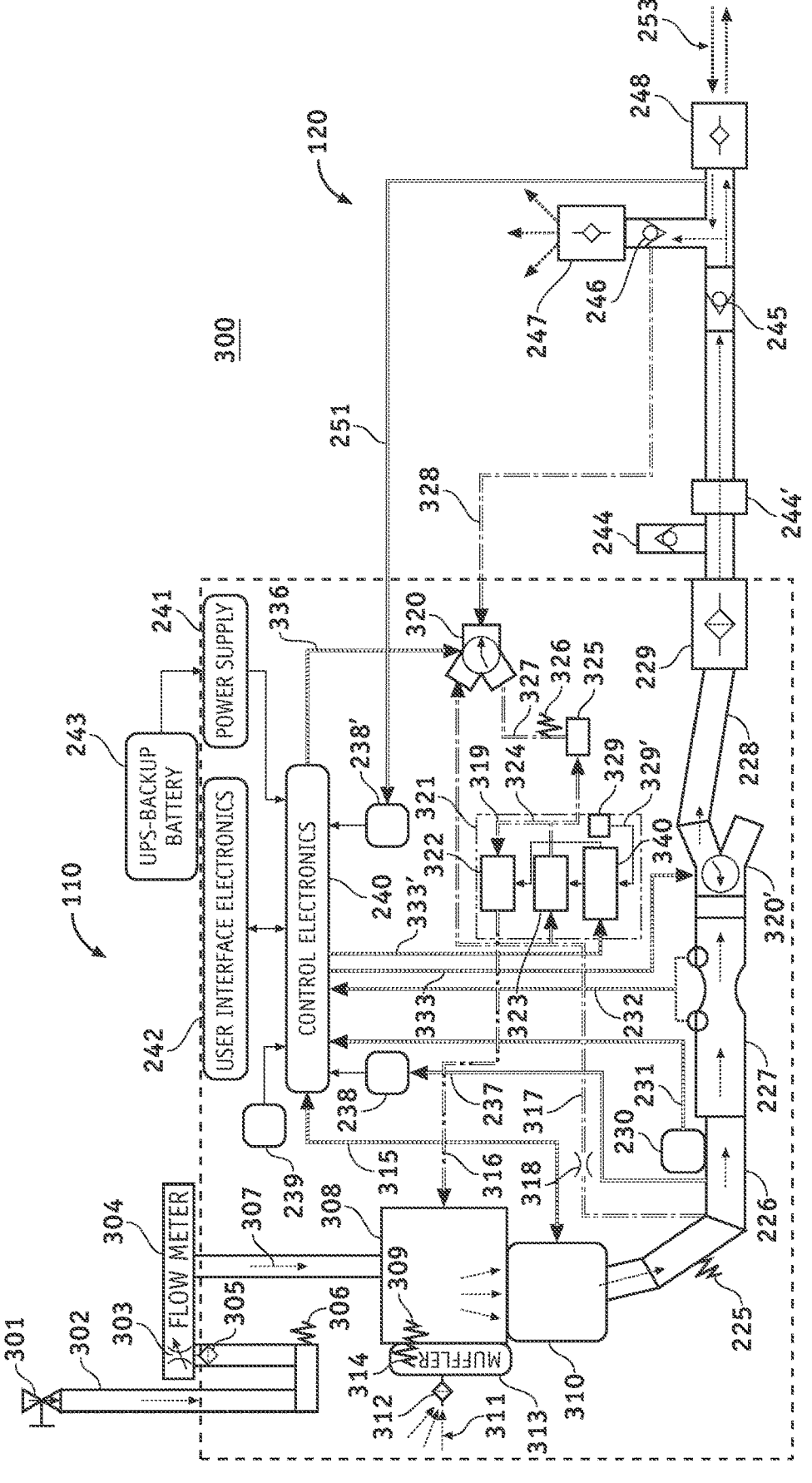
FIG. 3A shows an exemplary medical system according to a blower type embodiment of the present disclosure
Figure 3B:
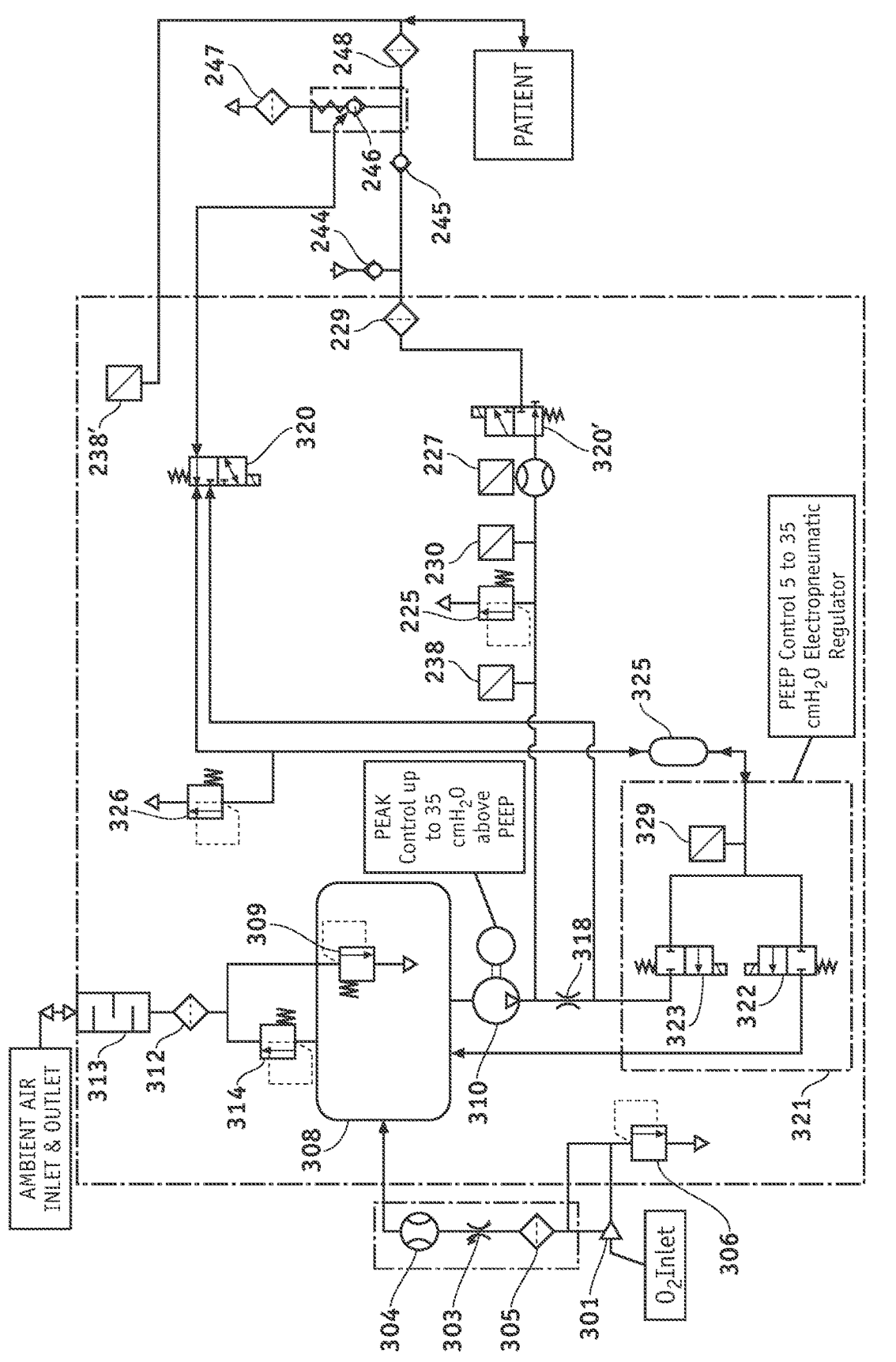
FIG. 3B shows the fluid schematic diagram of the exemplary medical system of FIG. 2A.

FIG. 3A shows an exemplary medical system (300) in accordance with an another embodiment of the present disclosure, where a blower type ventilator is described. The fluid schematic diagram of the medical system (300) is shown in FIG. 3B. As FIG. 3B represents a fluid schematic diagram, some of the elements shown in FIG. 3A are not shown in FIG. 3B. Comparing the embodiments of FIGS. 3A-3B with those of FIGS. 2A-2B, the elements with the same numerals are intended to provide the same functionalities in both sets of embodiments.

FIGS. 3A-3B essentially represent another embodiment of elements (110, 120) of FIG. 1 together with the constituents of such elements, the detailed description of which is given in what follows. Such embodiment can be generally adopted in cases where medical grade air is not available at the facility where the ventilator is intended to be used.

Referring to FIGS. 3A-3B, pressurized oxygen is supplied by the facility and is regulated by regulator (301). The regulated oxygen then enters ventilator (110) through hose (302) to then pass through particulate filter (305), needle valve (303), flow meter (304) and hose (307) to flow towards downstream of ventilator (110). Particulate filter (305) may be a 60 um filter which is used to filter out unwanted particulates from the oxygen. In accordance with embodiments of the present disclosure, needle valve (303) and flow meter (304) may be implemented in the same assembly.

The ventilator (110) of FIGS. 3A-3B comprises an input plenum (308) connected at one side to blower (310) comprising a motor (not shown), and to muffler (313) at another side. The function of the muffler (313) is to suppress the noise generated by ventilator (110) during operative conditions. As shown by arrows (311), after passing through particulate filter (312) and muffler (313), non-pressurized ambient air, taken e.g. from the facility, enters the input plenum (308). Muffler (313) comprises relief valve (314) to assure the pressure inside muffler (313) remains below a safe limit. Particulate filter (312) may be a 90 um filter which is used to filter out unwanted particulates from the received air. Input plenum (308) comprises relief valve (309) and essentially functions as a blender. In operative conditions when blower (310) is running, thus generating a negative pressure inside input plenum (308), the unpressurized air from the facility, and the pressurized oxygen flowing towards the input plenum (308) through hose (307) are sucked in the input plenum (308) and blended, thus generating a mixture of air and oxygen. As will be described more in detail later, such mixture is then supplied, through blower (310), inside ventilator (110) and then to the rest of the system downstream of ventilator (110), thereby providing the patient with the required oxygen.

Similarly to what previously described with regards to FIGS. 2A-2B, FIO2 sensor (230) is placed at sensor manifold (226) to measure the percentage of the oxygen in the inspired air that may be required to be, for example, within a desired range of 21%-100%. Such measured percentage is sent to control electronics (240) via electrical connection (231) and then communicated to user interface electronics (242) to be displayed on an external panel of ventilator (110). Based on the displayed measurement, the operator may decide to change the oxygen level by way of adjusting a knob (not shown) connected to needle valve (303) until the desired oxygen percentage level in the mixture is achieved. Additionally, by way of example, and not of limitation, relief valve (309) of FIGS. 3A-3B may be a 2 cm H2O relief valve. In other words, based on such example, a pressure of at least 2 cm H2O is required by relief valve (309) to open and let air flow inside input plenum (308). This means that precedence is given more to oxygen than to air when blending them in the mixture. The main reason for such precedence is that in most cases the patients assisted with these ventilators are in critical conditions, thus requiring a higher level of oxygen in the mixture.

Ventilator (110) of FIGS. 3A-3B further comprises electro-pneumatic regulator (321) which essentially serves to control the desired pressure level of the air/oxygen mixture supplied to the patient during both the inspiration and the expirations phases. Electro-pneumatic regulator (321) comprises regulator electronics (340), first 2-way valve (323), second 2-way valve (322), and pressure sensor (329). In operative connection with the electro-pneumatic regulator (321), the ventilator (110) further comprises reservoir (325), a first 3-way selector valve (320) and a second 3-way selector valve (320'). The output of first 2-way valve (323), the input of the second 2-way valve (322) and reservoir (325) are connected together via hose (324). The input of the first 2-way valve (323) and the normally closed (NC) section of the 3-way selector valve (320) are connected to FIO2 sensor manifold (226) through hose (317). Orifice (318) is used to adjust the flow in hose (317). Orifice (318) may be a ⅛" orifice. The output of the second 2-way valve (322) is connected to input plenum (308) via hose (316). Regulator electronics (340) is electrically connected to pressure sensor (329) and to control electronics (240) via electrical connections (329', 333') respectively. Based on the above-mentioned fluidical and electrical connections, the pressure at reservoir (329) is controlled to match the desired pressure to be supplied to the patient during the operative conditions. This is described more in detail in what follows.

With reference to FIG. 3A, control electronics (240) communicates the desired pressure to regulator electronics (340) via electrical connection (333'). Moreover, the pressure inside hose (319), representing the pressure of reservoir (325), is measured by pressure sensor (329) and communicated to regulator electronics (340). Based on a comparison of the measured and desired pressure, regulated electronics (340) controls the first 2-way valve (323) to further open or close, thereby adjusting the pressure of reservoir (325) and therefore the pressure of the gas supplied to the patient. In cases where the pressure of reservoir (325) surpasses the desired pressure, regulator electronics (340) controls the second 2-way valve (322) to further open, thereby flushing the extra pressure of reservoir (325) into input plenum (308) via hose (316). The first 3-way selector (320) is also connected via pilot hose (328) to expiratory valve (246) on the patient side. Similarly to what previously described with regards to FIGS. 2A, the states of the first and the second 3-way selector valves (320, 320') are controlled by control electronics (240) via electrical connections (336, 333) respectively. During the inspiration phase, both the first and the second 3-way selector valves (320, 320') are in closed state and during the expiration phase they are both in open state. As a result, the pressure supplied to the patient side is maintained as desired during both the inspiratory (PIP) and the expiratory (PEEP) phases. Upon transition from the inspiration to the expiration phase, the extra pressure from pilot hose (328) is flushed through the first 3-way selector valve (320) to reservoir (325). This means, in contrast with the embodiment of FIG. 2A, that there is no need for bleeding orifice (224) of FIG. 2A to blow air to the outside environment anymore during the transition from the inspiration to the expiration phase, and that's why, as can be noticed in FIG. 3A, the normally open section of the second 3-way selector valve (320') is blocked. Control electronics (240) may also be electrically connected to blower (310) via electrical connection (315) to control the blower (310) such that a desired pressure is supplied by blower (310). In order to perform such control, during operative conditions, the speed of the motor inside the blower (310) is measured and transmitted to control electronics (240). Based on a combination of the measured motor speed and the measured pressure received from pressure sensor (238), the control electronics (420) transmits a control command to adjust the motor speed, thereby tracking the desired pressure.

With continued reference to FIGS. 3A-3B, ventilator (110) further comprises a relief valve (306), which may be a 100 psi relief valve, and a relief valve (326), which may be 0.03 psi relief valve with similar functionality of protecting the system from unwanted higher pressures. Aside from what was described above, the rest of the functionalities of the embodiments of FIGS. 3A-3B, is similar to what was described previously with regards to the embodiments of FIGS. 2A-2B.

Referring again to FIGS. 3A-3B, input plenum (308) intakes room air through relief valve (309) that has, for example, a 2 cmH2O pressure drop upon entering input plenum (308). Additionally, oxygen is fed into input plenum (308) through flow control needle valve (303). The air entering input plenum (308) is always, for example, 2 cmH2O less than atmospheric pressure due to pressure relief valve (309) that the air pass through to get into input plenum (308). The blower motor demands a certain amount of air flow through input plenum (308) to meet the downstream demand of the ventilation process. Without oxygen flow into input plenum (308), all of the flow demand from the blower fan is provided by the intake air. As oxygen flow is added to input plenum (308), the difference in demand above the oxygen flow is made up with air from the intake. Once the oxygen flow matches the demand, no air flow will be drawn into input plenum (308) due to the presence of the relief valve (309). If the oxygen flow is increased above the blower fan demand, a separate set of relief valves (not shown) allows the excess oxygen to vent from the plenum out to the room. Quick surges in flow demand will result in the maximum percentage of oxygen in the blended air being slightly less than 100%. This is solved by using a larger plenum.

Figure 3C:
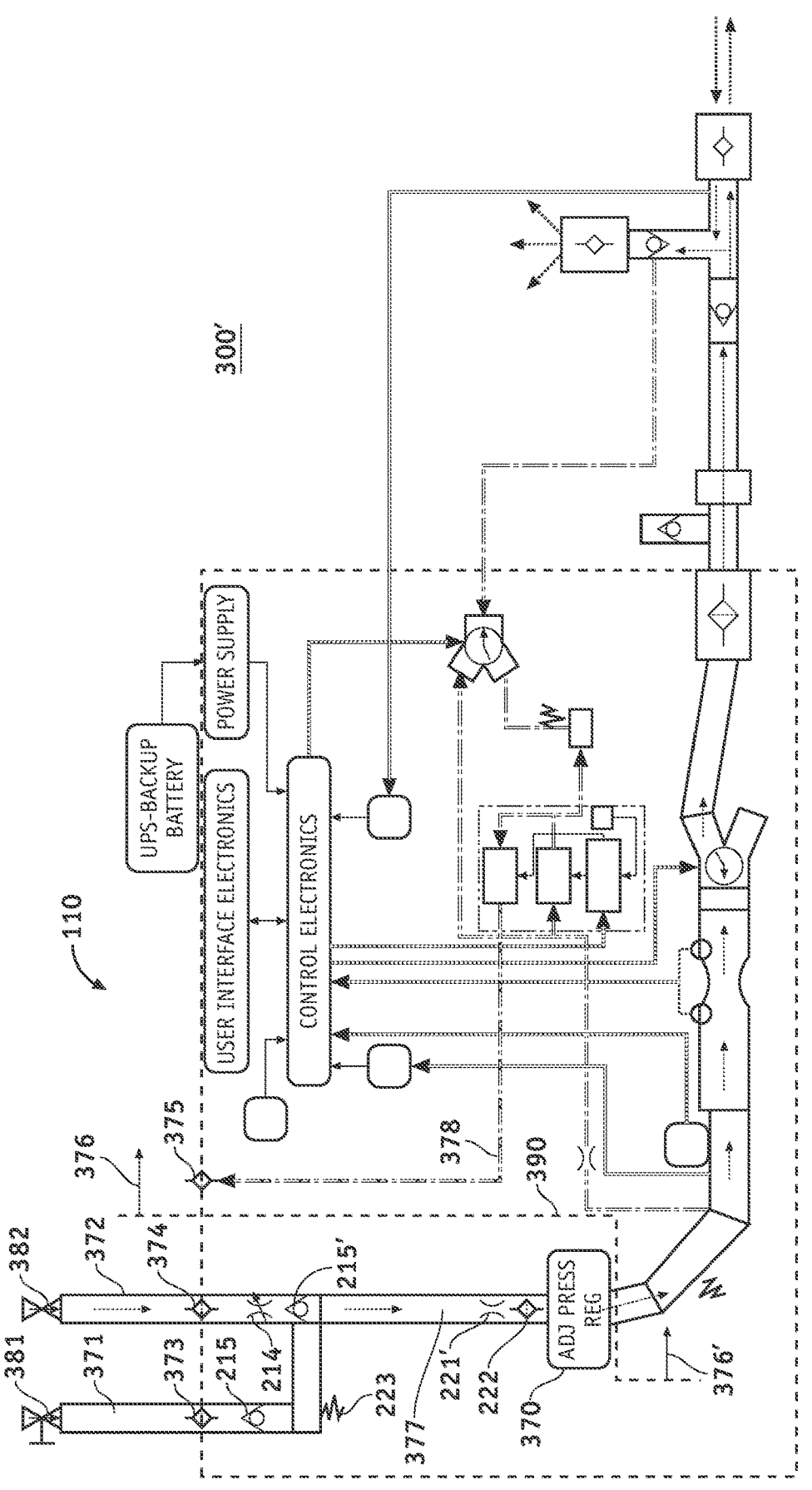
FIG. 3C shows an exemplary medical system according to a pneumatic type embodiment of the present disclosure.

FIG. 3C shows another exemplary medical system (300') according to a pneumatic type embodiment of the present disclosure. As shown, the functionalities of the elements on the right hand side of the dashed line (390), as also indicated by arrows (376, 376'), are similar to what previously described with regards to the same elements shown in FIG. 3B. For the sake of simplicity such similar elements are not annotated in FIG. 3C.

With reference to FIG. 3C, regulated pressurized oxygen is supplied through oxygen supply (381) and regulated pressurized air is supplied through air supply (382). The oxygen and air supplies (381, 382) may be provided, for example, by the medical facility. Supplied oxygen and air flow through tubes (371, 372) before getting mixed and the mixture is then received by an adjustable pressure regulator (370) which may be adjusted manually by the operator. The functionality of the pressure regulator (370) is to provide the required mixture pressure downstream to the patient. The role of elements (241, 215, 215') is similar to what was previously described with regards to same elements in FIG. 2A. Tubes (371, 372) further include particulate filters (373, 374) which are served to remove undesired particulates from the supplied air and oxygen.

With further reference to FIGS. 3B-3C, as mentioned before, all the elements shown on the right hand side of the dashed line (390) have similar functionalities with the same elements as shown in FIG. 3B. The only difference is that when the second 2-way valve (322) is in open state to relief the excess pressure of reservoir (325), the excess gas inside the reservoir (325) is flushed to the outside environment through hose (378) and exhaust filter (375). This is in contrast with the case of embodiment of FIG. 3B wherein the excess gas is flushed into input plenum (308).

Figure 4:
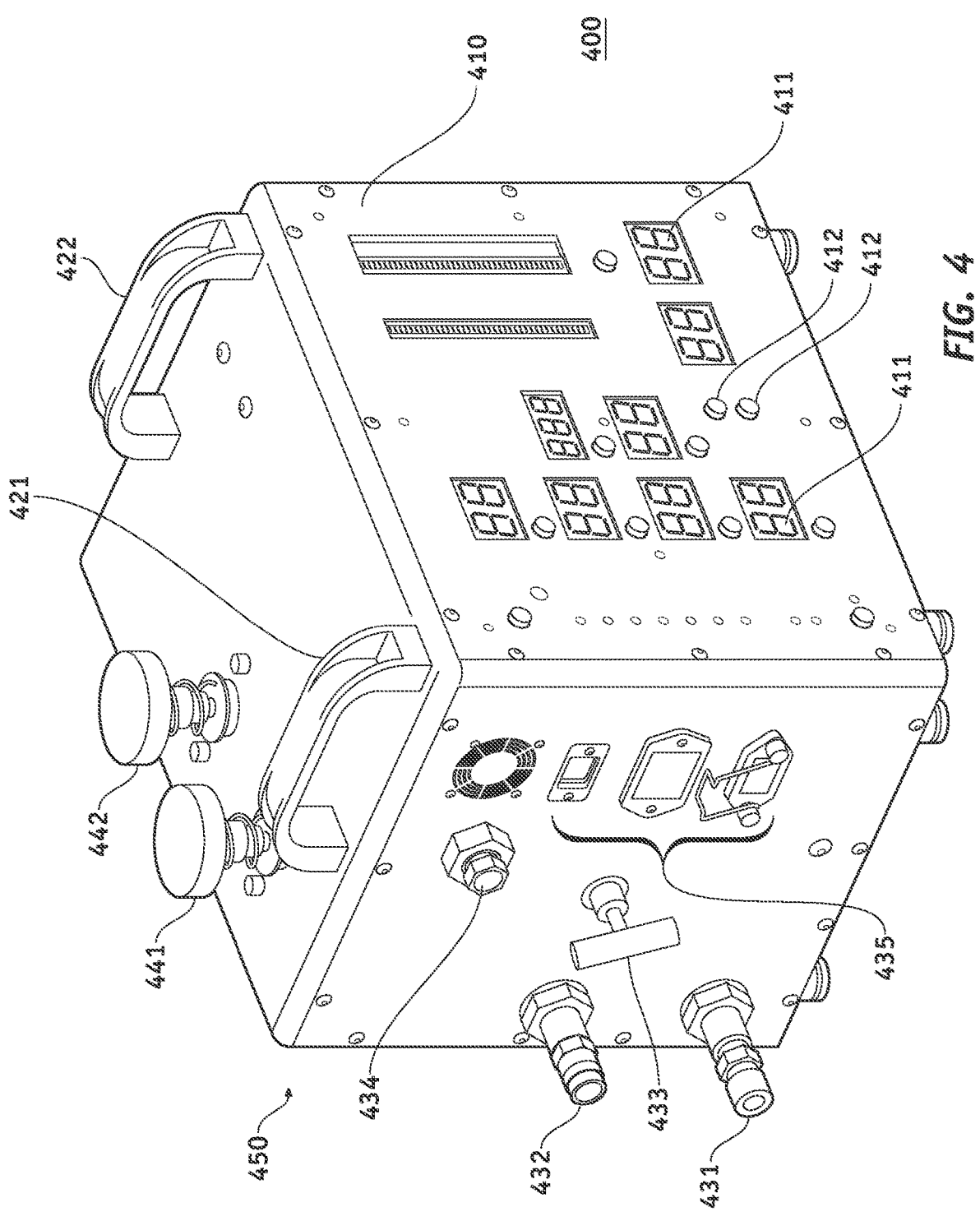
FIG. 4 shows a three-dimensional view of an exemplary ventilator in accordance with embodiments of the present disclosure.

FIG. 4 shows a three-dimensional view of an exemplary ventilator (400) in accordance with embodiments of the present disclosure. Ventilator (400) comprises user interface (410) including displays (411) and buttons (412). Also shown in FIG. 4 are lifting handles (421, 422) used for carrying the ventilator. There are three manual knobs (441, 442, 433) that are used by the operator to manually set the desired PEEP pressure, PIP pressure and the desired oxygen percentage. Oxygen inlet (431) is used to receive oxygen from the facility regulator and ail inlet (432) is used to receive air from the facility air regulator. Ventilator (400) further comprises blended gas breather vent (434) and AC/DC/USB plugins (435). It should be noted that the inventive design of the elements and their disposition as shown in the diagrams and descriptions of FIGS. 2A-2B and 3A-3C allows for a much more compact and portable design that prior ventilators known to the inventors.

Figure 5:
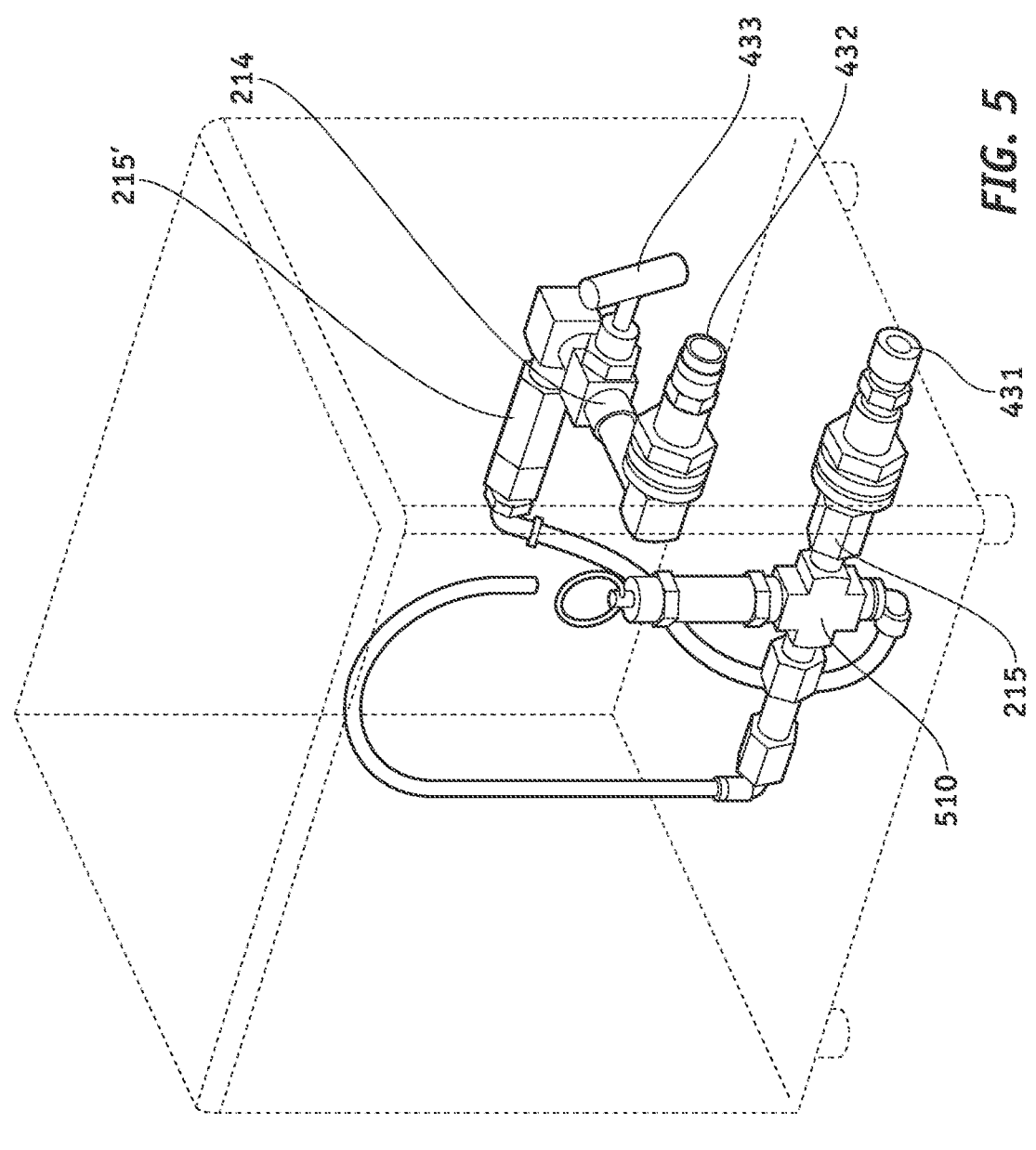
FIG. 5 shows some exemplary constituents of the ventilator of FIG. 4 according to embodiments of the present disclosure.

FIG. 5 shows an inside view of ventilator (400) of FIG. 4 to show some constituents related to the blending of oxygen and air with reference to the pneumatic type embodiment of FIGS. 2A, 2B and 3C. With reference to FIGS. 2A and 5, supplied air coming in through oxygen inlet (431) passes through check valve (215) to flow inside blender (510). Supplied air coming through air inlet (432) passes through adjustable orifice (214) and check valve (215') to also flow into blender (510) where air and oxygen are blended. As described previously, manual knob (433) is used to adjust orifice (214), thereby matching the oxygen percentage to a desired value. In accordance with embodiments of the present disclosure, check valves (215, 215') may be 5 psi and 0.1 psi check valves respectively.

Main Modes of Operation

According to embodiments of the present disclosure, in normal operative conditions, the ventilator (110) shown in FIGS. 1 and 2A-2B can operate in at least two different modes, indicated as mandatory mode and spontaneous mode. The mandatory mode is preferably used in scenarios where the patient is sedated or in critical condition and cannot breathe on their own. In this mode of operation, the operator can manually set the breathing rate that is desired to take place. The corresponding parameter is called the backup rate. Using a combination of the backup rate and other parameters (also manually set by the operator) such as the inspiratory rate or the inspiratory/expiratory ratio, the ventilator will execute the inspiration and expiration phases. In accordance with the teachings of the present disclosure, ventilator (110) provides an inspirational flow rate such that the integral of the inspiratory flow rate over the inspiration time matches the desired tidal volume which can also be manually set by the operator. In other words, the breathing is controlled based on a specified tidal volume and breathing rate.

Turning now to the spontaneous mode, also the patient is breathing while being connected to the system and being supplied with extra oxygen/air. In other words, in the spontaneous mode, the system provides pressure support for those patients breathing to some extent by themselves. During such mode of operation, the inspiration is triggered when one of the followings occurs: a) the patient initiates a spontaneous inspiration, or b) when the pressure on the patient side drop below the PEEP pressure. With reference to FIGS. 2A-2B, and as mentioned previously, the pressure on the patient side is measured through a combination of plateau tube (251) and plateau pressure sensor (238'). As also described previously, after receiving such a measurement, control electronics (240) will issue control signals through electrical connections (236, 233), to 3-way selector valves (220, 220') respectively, to change the state of such valves from open to close, thus transitioning the system from expiratory phase to inspiratory phase.

Control Software

Figure 6:
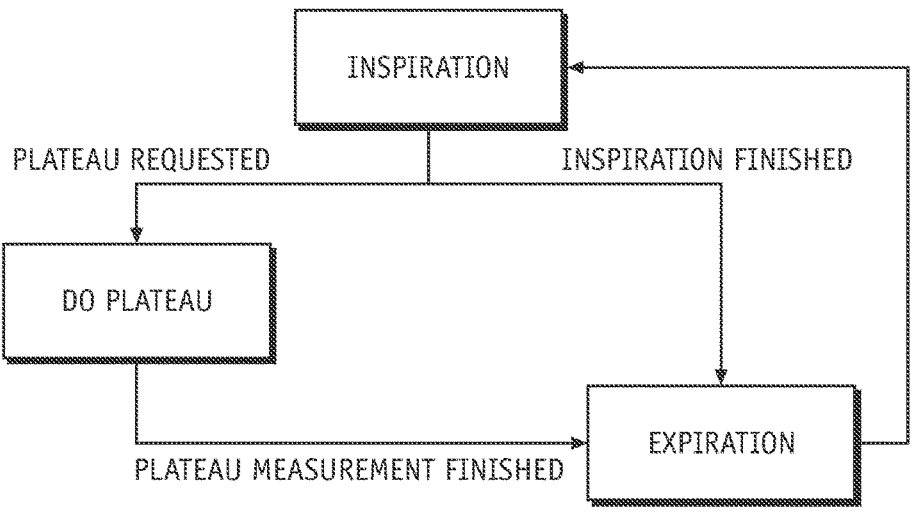
FIG. 6 shows an exemplary flow of the inspiration and the expirations phases according to embodiments of the present disclosure.

As shown in FIG. 6, during a normal operative condition, the system is controlled by an embedded control software operating in conjunction with the control electronics (240) previously described in FIG. 2A to cycle through consecutive inspiration and expiration phases. In accordance with the teachings of the present disclosure, regardless of what modes of operation the system is implementing, the inspiratory phase may also be interrupted by the operator requesting, through the user interface, to take a plateau-pressure measurement. This is also illustrated in FIG. 6. After receiving this request, the system performs the requested measurement and transitions to a new expiratory phase.

Figure 7:
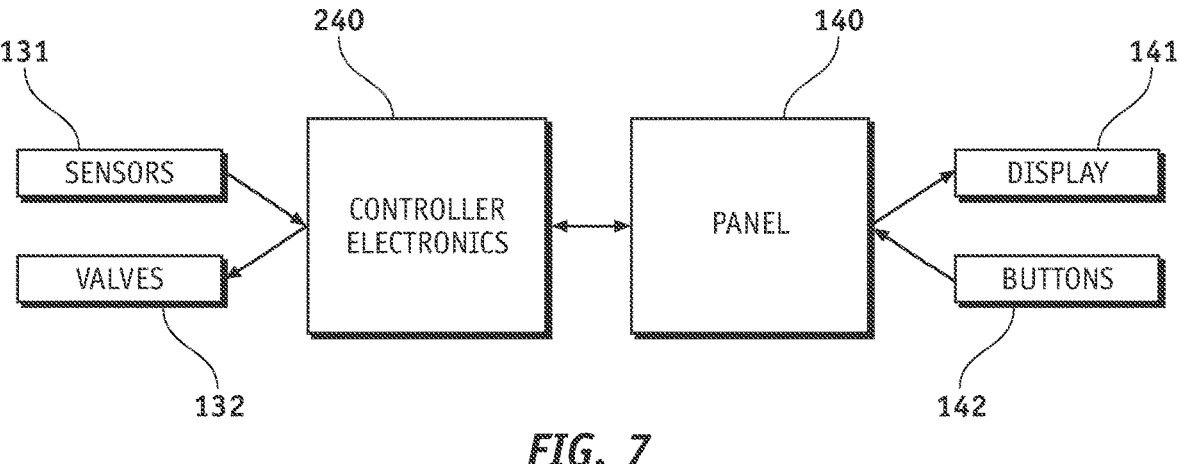
FIG. 7 shows a block diagram illustrating exemplary interactions of various constituents of a ventilator according to embodiments of the present disclosure.

With reference to FIGS. 1, 2A-2B, the overall operation of medical system (100) is controlled through the above-mentioned control software interacting with control electronics (240) and user interface electronics (242). FIG. 7 illustrates such an interaction. Panel (140), display (141) and buttons (142) are parts of the user interface. In what follows, the portion of the control software talking to control electronics (240) will be indicated as controller software, while the portion of the control software interacting with the user interface including panel (140), display (141), and buttons (142) will be indicated as panel software.

Referring to FIG. 7, through interaction with controller electronics (240), the controller software is tasked with reading the sensors (131) and operating the air flow valves (132). On the other hand, through interaction with user interface electronics (242) and the user interface, the panel software is tasked with updating displays (141) and receiving operator inputs. The panel software manages the set points for various values in the system and sends these parameters to the controller software which in turn uses these parameters to operate the valves (132) and responds to the panel (140) with the sensor (131) readings. The panel software uses these sensor readings to update live displays (141) as well as set alarms, should these readings violate established alarm conditions.

Figure 8A:
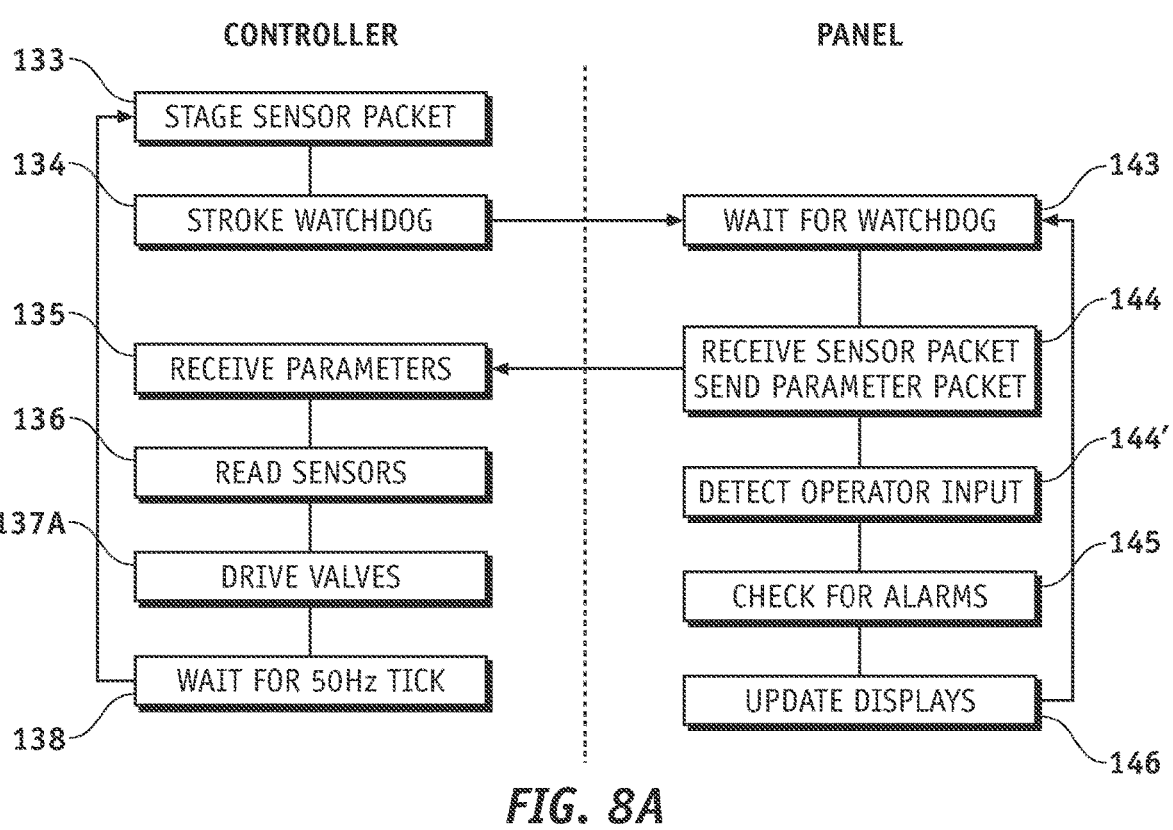
FIGS. 8A-8B show high-level flows of an exemplary control software according to embodiments of the present disclosure in case of a pneumatic type ventilator and a blower type ventilator, respectively.
Figure 8B:
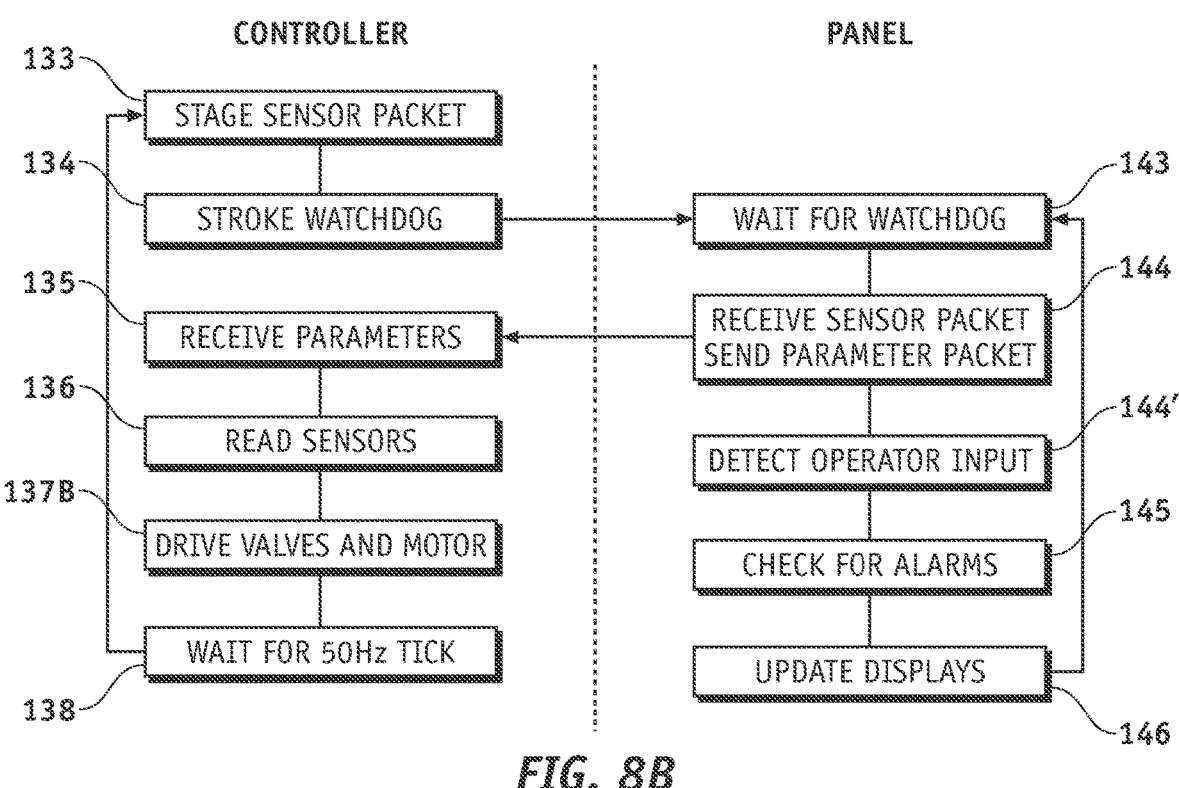

FIGS. 8A-8B shows a high-level flow of the overall control software, both on the controller and on the panel side. FIG. 8A applies to the pneumatic type embodiments of FIGS. 2A-2B, and FIG. 8B applies to the blower type embodiments of FIGS. 3A-3B. The only different between the two flows of FIGS. 8A-8B are steps (137A, 137B), where step (137B) includes also the control of the motor. The whole process can be performed, for example, in a 50 Hz loop. The controller software stages the data, i.e. the outgoing packet (step 133) and then toggles its watchdog (step 134) enabling the panel software to conduct a send/receive transaction, i.e. bidirectional communication. Staged sensor data is sent to the panel software and the operator specified values are sent to the controller software (steps 144, 144', 135). These transactions happen at the same time. The controller then reads sensors and takes the incoming operator specified values (step 136), controls outputs (step 137A), or control output and motor (step 137B), and then waits for the next tick of the 50 Hz clock (step 138). The panel software reads buttons, checks for tripped alarms (145), and sets the displays (146) before waiting for the next 50 Hz watchdog (143) from the controller. Multiple 50 Hz cycles occur during a full inspiration/expiration phase.

According to an embodiment of the present disclosure, the control software may run on a STM32 microprocessor, e.g. STM32F051C8T6TR microcontroller. This is a 32-bit ARM architecture embedded processor with a little-endian memory architecture.

A number of embodiments according to the present disclosure have been described. It is to be understood that various modifications may be made without departing from the spirit and scope of such embodiments. For example, some of the steps described above may be order indepen-
dent, and thus can be performed in an order different from
that described. Further, some of the steps described above
may be optional. Various activities described with respect to
the methods identified above can be executed in repetitive,
serial, or parallel fashion.

It is to be understood that the foregoing description is
intended to illustrate and not to limit the scope of the
disclosure, which is defined by the scope of the following
claims, and that other embodiments are within the scope of
the claims. (Note that the parenthetical labels for claim
elements are for ease of referring to such elements, and do
not in themselves indicate a particular required ordering or
enumeration of elements; further, such labels may be reused
in dependent claims as references to additional elements
without being regarded as starting a conflicting labeling
sequence).

The invention claimed is:

1. A lung ventilator comprising:
a blender, and
a pressure and/or flow regulation section comprising a
first pressure regulator and a second pressure regulator;
wherein:
the blender is configured to separately receive oxygen in
a regulated oxygen flow from an oxygen source and air
in a regulated air flow from an air source, and to blend
the oxygen and the air to provide a blended gas;
the pressure and/or flow regulation section is configured
to receive the blended gas from the blender and to
regulate the blended gas to a first pressure by the first
pressure regulator and to a second pressure by the
second pressure regulator, the first pressure being a
peak inspiratory pressure (PIP) and the second pressure
being a positive end-expiratory pressure (PEEP);
the first pressure regulator is an adjustable first pressure
regulator and the second pressure regulator is an adjust-
able second pressure regulator;
the pressure and/or flow regulation section further com-
prises:
a first selector connected downstream of the first pressure
regulator and the second pressure regulator and con-
figured to select and direct the blended gas at the first
pressure or at the second pressure; and
a second selector connected downstream of the first
selector and in fluid communication therewith, the
second selector being configured to receive the selected
blended gas and in a transmit state to transmit the
selected blended gas downstream of the ventilator and
in a block state to block the selected blended gas.

2. The lung ventilator of claim 1, wherein the first selector
and/or the second selector are a three-way valve.

3. The lung ventilator of claim 1, further comprising a
selector connection hose connecting the first selector with
the second selector.

4. The lung ventilator of claim 1, further comprising a
control circuit configured to control a state of the first
selector and the second selector.

5. The lung ventilator of claim 4, further comprising a
user interface connected with the control circuit, the user
interface comprising:
a plurality of displays to display measured parameter
values, and
a plurality of buttons to enter desired parameter values.

6. The lung ventilator of claim 5, wherein the blender
further comprises a variable orifice adjustable by a button of
the plurality of buttons, and wherein during operative conditions the variable orifice is adjusted as a function of the
oxygen percentage measured value.

7. The lung ventilator of claim 5, wherein during opera-
tive conditions, the control circuit is configured to calculate
a tidal volume based on an integral of the measured flow rate
over an inspiration time, the tidal volume being displayed on
a tidal volume display of the plurality of displays.

8. The lung ventilator of claim 4, further comprising a
static pressure sensor electrically connected to the control
circuit and fluidically connected to a point downstream of
the second selector with a stagnant flow, the static pressure
sensor configured to measure a static pressure during opera-
tive conditions.

9. The lung ventilator of claim 4, further comprising a
plateau pressure sensor electrically connected to the control
circuit and configured to be fluidically connected to a
detachable patient-specific device, the plateau pressure sen-
sor being configured to measure a plateau pressure during
the expiration phase.

10. The lung ventilator of claim 4, further comprising
embedded software including i) controller software config-
ured to manage the control circuit and ii) panel software to
manage the displays.

11. The lung ventilator of claim 10, wherein the controller
software is configured to interact with the panel software by
sending sensed data to the panel software for displaying
purposes and by receiving from the panel software operator
specified values.

12. The lung ventilator of claim 11, wherein the controller
software is configured to control the first selector valve and
the second selector valve as a function of the sensed data and
the operator specified values.

13. The lung ventilator of claim 1, wherein the first
selector and the second selector each have an independently
controllable first state and second state.

14. The lung ventilator of claim 13, wherein:
in an inspiration phase, the first and the second selector
valves are both in the first state, thereby letting the
blended gas at the first pressure (PIP) flow downstream
of the ventilator, and
in an expiration phase, the first selector is in the second
state and the second selector is in the first state, thereby
letting the blended gas at the second pressure (PEEP)
flow downstream of the ventilator.

15. The lung ventilator of claim 13, wherein the first
selector has an independently controllable first state and
second state, wherein the first state is a state in which the
first selector directs the blended gas at the first pressure (PIP)
to the second selector and the second state is a state in which
the first selector directs the blended gas at the second
pressure (PEEP) to the second selector.

16. The lung ventilator of claim 1, further comprising a
flow/pressure measurement section placed downstream of
the second selector.

17. The lung ventilator of claim 16, the flow/pressure
measurement section comprising:
a fractional inspired oxygen (FIO2) sensor configured to
measure a percentage of inspired oxygen and to gen-
erate an oxygen percentage measured value, and
a differential pressure flow sensor configured to measure
a flow rate based on a differential pressure measure-
ment and to generate a flow rate measured value.

18. A lung ventilator comprising:
a blender, and
a pressure and/or flow regulation section comprising a
first pressure regulator and a second pressure regulator;
wherein:

the blender is configured to separately receive oxygen in a regulated oxygen flow from an oxygen source and air in a regulated air flow from an air source, and to blend the oxygen and the air to provide a blended gas;

the pressure and/or flow regulation section is configured to receive the blended gas from the blender and to regulate the blended gas to a first pressure by the first pressure regulator, the first pressure being a peak inspiratory pressure (PIP), and to regulate the blended gas to a second pressure by the second pressure regulator, the second pressure being a positive end-expiratory pressure (PEEP);

the pressure and/or flow regulation section further comprises:

a first selector connected downstream of the first pressure regulator and the second pressure regulator and configured to select the blended gas at the first pressure or at the second pressure;

a second selector connected downstream of the first selector;

a selector connection hose fluidically connecting the first selector to the second selector; and a pilot hose fluidically connected at a first end to the selector connection hose and configured at a second end for connection to a patient-specific device.

19. The lung ventilator of claim 18, wherein the second selector is configured to change state from the first state to the second state upon transition from the inspiration phase to the expiration phase, to relieve pressure from the pilot hose by letting extra gas flow out of the lung ventilator.

20. The lung ventilator of claim 19, wherein the extra gas flow is let out of the lung ventilator through a bleed orifice of the second selector.

* * * * *